(12) United States Patent
Bazan et al.

(10) Patent No.: US 8,729,128 B2
(45) Date of Patent: May 20, 2014

(54) LIPOXIN A4 PROTECTION FOR CORNEA ENDOTHELIAL CELLS

(75) Inventors: Nicolas G. Bazan, Baton Rouge, LA (US); Jiu-Cheng He, Baton Rouge, LA (US); Haydee E. P. Bazan, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 789 days.

(21) Appl. No.: 12/740,413

(22) PCT Filed: Oct. 30, 2008

(86) PCT No.: PCT/US2008/081723
§ 371 (c)(1),
(2), (4) Date: Jul. 23, 2010

(87) PCT Pub. No.: WO2009/058958
PCT Pub. Date: May 7, 2009

(65) Prior Publication Data
US 2011/0009488 A1 Jan. 13, 2011

Related U.S. Application Data

(60) Provisional application No. 60/983,760, filed on Oct. 30, 2007.

(51) Int. Cl.
*A61K 31/557* (2006.01)
*A61K 31/185* (2006.01)

(52) U.S. Cl.
USPC .......................... 514/573; 514/553; 514/912

(58) Field of Classification Search
USPC ......................... 514/553, 557, 912
See application file for complete search history.

(56) References Cited

U.S. PATENT DOCUMENTS

| | | | |
|---|---|---|---|
| 5,051,443 A | 9/1991 | Neufeld et al. | 514/420 |
| 6,645,978 B1 | 11/2003 | Gamache et al. | 514/310 |
| 6,831,186 B2 | 12/2004 | Bauman et al. | 554/376 |
| 2005/0255144 A1 | 11/2005 | Schultz | 424/428 |

OTHER PUBLICATIONS

Bannenberg, G. et al., "Lipoxins and novel 15-epi-lipoxin analogs display potent anti-inflammatory actions after oral administration," Brit. J. Pharma. vol. 143, pp. 43-52 (2004).
Bazan, N., "Metabolism of Arachidonic Acid in the Retina and Retinal Pigment Epithelium: Biological Effects of Oxygenated Metabolites of Arachidonic Acid," The Ocular Effects of Prostaglandins and Other Eicosanoids, Pub. Alan R. Liss, Inc., pp. 15-37 (1989).
Bazan, N. et al., "Signal Transduction and Gene Expression in the Eye: A Contemporary View of the Pro-inflammatory, Anti-inflammatory and Modulatory Roles of Prostaglandins and Other Bioactive Lipids," Survey of Opth., vol. 41, Supp.2, pp. S23-S34 (1997).
Bazan, N. et al., "Arachidonic Acid Cascade and Platelet-Activating Factor in the Network of Eye Inflammatory Mediators: Therapeutic Implications in Uveitis," Int'l Opth., vol. 14, pp. 335-344 (1990).
Bazan, N.G.,"Eicosanoids, Docosanoids, Platelet-Activating Factor and Inflammation," In Basic Neurochemistry: Molecular, Cellular and Medical Aspects, 7th edition, G.Siegel et al. (eds.), Chapter 33, pp. 575-591 (2006).
Fierro, I.M. et al., "Lipoxin A4 and aspirin-triggered 15-epi-lipoxin A4 inhibit human neutrophil migration: Comparisons between synthetic 15 epimers in chemotaxis and transmigration with microvessel endothelial cells and epithelial cells," Journal of Immunology, vol. 170, pp. 2688-2694 (2003).
Fiorucci, S. et al., "A β-oxidation-resistant lipoxin $A_4$ analog treats hapten-induced colitis by attenuating inflammation and immune dysfunction," Proc. Natl. Acad. Sci. USA, vol. 101, No. 44, pp. 15736-15741 (2004); with Editorial Expression Update: PNAS, vol. 105, No. 22, p. 7892 (2008).
Gronert, K. et al., "A role for the mouse 12/15-lipoxygenase pathway in promoting epithelial wound healing and host defense," PNAS, vol. 280, pp. 15267-15278 (2005).
Gronert, K. "Lipoxins in the eye and their role in wound healing," Prostaglandins, Leukotrienes and Essential Fatty Acids, vol. 73, pp. 221-229 (2005).
Mattson, M.P. et al., "Apoptosis and Necrosis," In Basic Neurochemistry: Molecular, Cellular and Medical Aspects, 7th edition, G.Siegel, R.W. Albers, S.T. Brady, D.L. Price (eds.), Chapter 35:603-615 (2006).
Scalia, R. et al., "Lipoxin $A_4$ stable analogs inhibit leukocyte rolling and adherence in the rat mesenteric microvasculature: role of P-selectin," Proc. Natl. Acad. Sci. USA, vol. 94, pp. 9967-9972 (1997).
Serhan, C.N. et al., "Aspirin-Triggered 14-Epi-Lipoxin $A_4$ and Novel Lipoxin $B_4$ Stable Analogs Inhibit Neutrophil-Mediated Changes in Vascular Permeability," Adv. Exp. Med. Biol., 469:287-293 (1999).
Nishimura, Julie K. et al., "Initial Endothelial Cell Density and Chronic Endothelial Cell Loss Rate in Corneal Transplants with Late Endothelial Failure," manuscript No. 98707, pp. 1962-1965, presented in part as poster at American Academy of Opthalmology annual meeting, New Orleans, Louisiana (Nov. 1998).
Thuret, Gilles et al., "Prospective, Randomized Clinical and Endothelial Evaluation of 2 Storage Times for Corneal Donor Tissue in Organ Culture at 31 ° C.," Arch. Opthalmol, vol. 121, pp. 442-450 (2003).

*Primary Examiner* — Zohreh Fay
(74) *Attorney, Agent, or Firm* — Bonnie J. Davis; John H. Runnels (57) ABSTRACT

Lipoxin A4 and its analogs have been discovered to promote the cell proliferation of cornea endothelial cells, and thus promote the proper functioning of the labile tissue layer of cornea endothelial cells. These lipoxin compounds can be administered alone or in combination with other known compounds as a solution that can be topically administered to decrease the swelling of the cornea or maintain the clarity of the cornea. Lipoxin A4 or its analogs can also be combined with other known nutritive compounds to form a solution for storage of a cornea prior to transplantation.

8 Claims, 8 Drawing Sheets

Fig. 2A

Epi-LXA4 Promotes Corneal Endothelial Proliferation in a dose-dependent fashion with the optimal concentrations of 50 to 100nM.

Fig. 2B

Epi-LXA4 Promotes Corneal Endothelial Proliferation in a dose-dependent fashion with the optimal concentrations of 50 to 100nM.

LIPOXIN A4 PROTECTION FOR CORNEA ENDOTHELIAL CELLS

The development of this invention was partially funded by the Government under grants numbered EY004928 and EY006635 from the National Institutes of Health National Eye Institute, and grant number P20 RR016816 from the National Institutes of Health National Center for Research Resources. The Government has certain rights in this invention.

This is the United States national stage of international application PCT/US2008/081723, international filing date Oct. 30, 2008, which claims the benefit of the filing date of provisional U.S. application Ser. No. 60/983,760, filed Oct. 30, 2007, under 35 U.S.C. §119(e).

TECHNICAL FIELD

This invention pertains to the use of lipoxin A4 and its analogs to prevent damage to the cornea endothelium and to promote the proliferation of corneal endothelium, for example, during the storage of corneas in eye banks or in corneas at risk from swelling or already swollen.

BACKGROUND ART

Cornea Endothelial Cells

Cornea endothelial cells are found at the boundary between the fluid-filled anterior chamber and the clear stroma at the posterior surface of the cornea. These cells are critical for the maintenance of the cornea, especially maintenance of its transparency and prevention of swelling. Improper functioning corneal endothelial cells are the root cause for the majority of corneal transplants. These cells are extremely fragile, and depend on maintaining a high cell population for proper repair mechanisms. If the number of cornea endothelial cells is low, the repair mechanisms may be insufficient to restore the endothelium and maintain the cornea in proper functioning state. Function of the cornea endothelium is restored when the endothelial cells again act as a proper permeability barrier and maintain the cornea in its clear, non-swollen state. The cornea endothelium is labile particularly during cornea storage prior to transplants, and many corneas need to be discarded due to loss of endothelial cells, when the corneas become swollen or lose clarity. Compositions and methods for enhancing and maintaining the human corneal endothelium are limited. See, U.S. Pat. No. 5,051,443.

Lipoxins

Lipoxins are biosynthesized from arachidonic acid. See, Bazan N. G. (2006) *In Basic Neurochemistry: Molecular, Cellular and Medical Aspects*, 7th edition, G. Siegel, R. W. Albers, S. T. Brady, D. L. Price (eds.), Chapter 33:575-591; and Mattson M. P., Bazan N. G. (2006) *In Basic Neurochemistry: Molecular, Cellular and Medical Aspects*, 7th edition, G. Siegel, R. W. Albers, S. T. Brady, D. L. Price (eds.), Chapter 35:603-615. Lipoxins are potent mediators of the resolution phase of the inflammatory response and of dysfunctional immunity. See, Serhan C. N., Takano T., Clish C. B., Gronert K., Petasis N. (1999) *Adv. Exp. Med. Biol.* 469: 287-293; and Fiorucci S., Wallace J. L., Mencarelli A., et al. (2004) *Proc. Natl. Acad. Sci. USA*. 101:15736-15741. Lipoxin A4 and its analogs, including lipoxin A4 epimer 15 (or 15-epi-lipoxin A4), are well known in the art. See, U.S. Pat. Nos. 6,831,186 and 6,645,978; I. M. Fierro et al., "Lipoxin A4 and aspirin-triggered 15-epi-lipoxin A4 inhibit human neutrophil migration: Comparisons between synthetic 15 epimers in chemotaxis and transmigration with microvessel endothelial cells and epithelial cells," Journal of Immunology, vol. 170, pp. 2688-2694 (2003); G. Bannenberg et al., "Lipoxins and novel 15-epi-lipoxin analogs display potent anti-inflammatory actions after oral administration," Brit. J. Pharma. Vol. 143, pp. 43-52 (2004); and R. Scalia et al., "Lipoxin A4 stable analogs inhibit leudocyte rolling and adherence in the rat mesenteric microvasculature: role of P-selectin," *Proc. Natl. Acad. Sci. USA*. vol. 94, pp. 9967-9'972 (1997). Lipoxin A4 and docosahexaenoic acid-derived neuroprotectin D1 (NPD1) are lipid autacoids formed by 12/15 lipoxygenase (LOX) pathways that exhibit anti-inflammatory and neuroprotective properties. Mouse corneal epithelial cells were found to generate both endogenous lipoxin A4 and NPD1. See, K. Gronert et al., A role for the mouse 12/15-lipoxygenase pathway in promoting epithelial wound healing and host defense," PNAS, vol. 280, pp. 15267-15278 (2005). Lipoxins have been reported to play a role in wound healing in the corneal of the eye. See, K. Gronert, "Lipoxins in the eye and their role in wound healing," Prostaglandins, Leukotrienes and Essential Fatty Acids, vol. 73, pp. 221-229 (2005). Lipoxin A4 was shown to be formed in the epithelium of healthy and injured corneas, and lipoxygenase (LOX) enzyme activity has been indicated in the cornea of rats and rabbits. In the mouse cornea, lipoxin A4 was found to be generated in the absence of inflammation. In other tissues, lipoxins are predominantly formed during the resolution phase of acute inflammation. (Gronert, 2005). Lipoxin A4 or LOX have not been reported from the cornea endothelial cells, or from any cells of the back of the eye, only from the corneal epithelial cells. See, also, Bazan, N. et al., "Signal Transduction and Gene Expression in the Eye: A Contemporary View of the Pro-inflammatory, Anti-inflammatory and Modulatory Roles of Prostaglandins and Other Bioactive Lipids," Survey of Opth., Vol. 41, Supp. 2, pp. S23-S34 (1997); Bazan, N. et al., "Arachidonic Acid Cascade and Platelet-Activating Factor in the Network of Eye Inflammatory Mediators: Therapeutic Implications In Uveitis," Int'l Opth., Vol. 14, pp. 335-344 (1990); and Bazan, N., "Metabolism of Arachidonic Acid in the Retina and Retinal Pigment Epithelium: Biological Effects of Oxygenated Metabolites of Arachidonic Acid," *The Ocular Effects of Prostaglandins and Other Eicosanoids*, Pub. Alan R. Liss, Inc., pp. 15-37 (1989

Lipoxin A4 and its analogs have been proposed as a treatment for dry eye, known generically as keratoconjunctivitis sicca and characterized by lack of moisture or lubrication in the eye. See, U.S. Pat. No. 6,645,978; and U.S. Patent Application Pub. No. U.S. 2005/0255144. Dry eye is known to be a separate condition from dry AMD, which is a disease of the back of the eye that involves the death of photoreceptors and RPE cells.

DISCLOSURE OF INVENTION

We have discovered that lipoxin A4 and its analogs enhance the survival and decrease cell apoptosis of cornea endothelial cells, and increase the number of endothelial cells that move into a wound area. These lipoxin compounds can be administered alone or in combination with other known compounds as a solution that can be topically administered to decrease the swelling of the cornea or maintain the clarity of the cornea. Lipoxin A4 or its analogs could also be combined with other known nutritive compounds to form a solution for storage of a cornea prior to transplanting it. Other compounds known to benefit the cornea endothelial cells are indomethacin, other non-steroidal anti-inflammatory compounds, and certain growth factors, e.g., epidermal growth factor. (U.S. Pat. No. 5,051,443) Nutritive compounds currently used for cornea storage consist, without limitation, of one or more of the following, chondroitin sulfate, a base, dextran 40, sodium bicarbonate, gentamycin (or other antibiotics), amino acids, sodium pyruvate, 2-mercaptoethanol. Some examples of these nutritive solutions are those made by Bausch & Lomb: OPTISOL®, OPTISOL GS™, DEXSOL™, AND MCCAREY-KAUFMAN™ Media.

This new cornea storage medium will preserve endothelial viability during a prolonged period of time at 4° C. as well as at 36° C. Endothelial viability is preserved by sustaining endothelial cell proliferation and maintenance of cell integrity. The cornea will be protected from swelling or loss of clarity. Also, because lipoxins inhibit apoptosis, they further promote endothelial cell survival.

MODES FOR CARRYING OUT THE INVENTION

Example 1

Corneal Endothelial Cells Possess Lipoxin A4 Receptors

Figure 1:
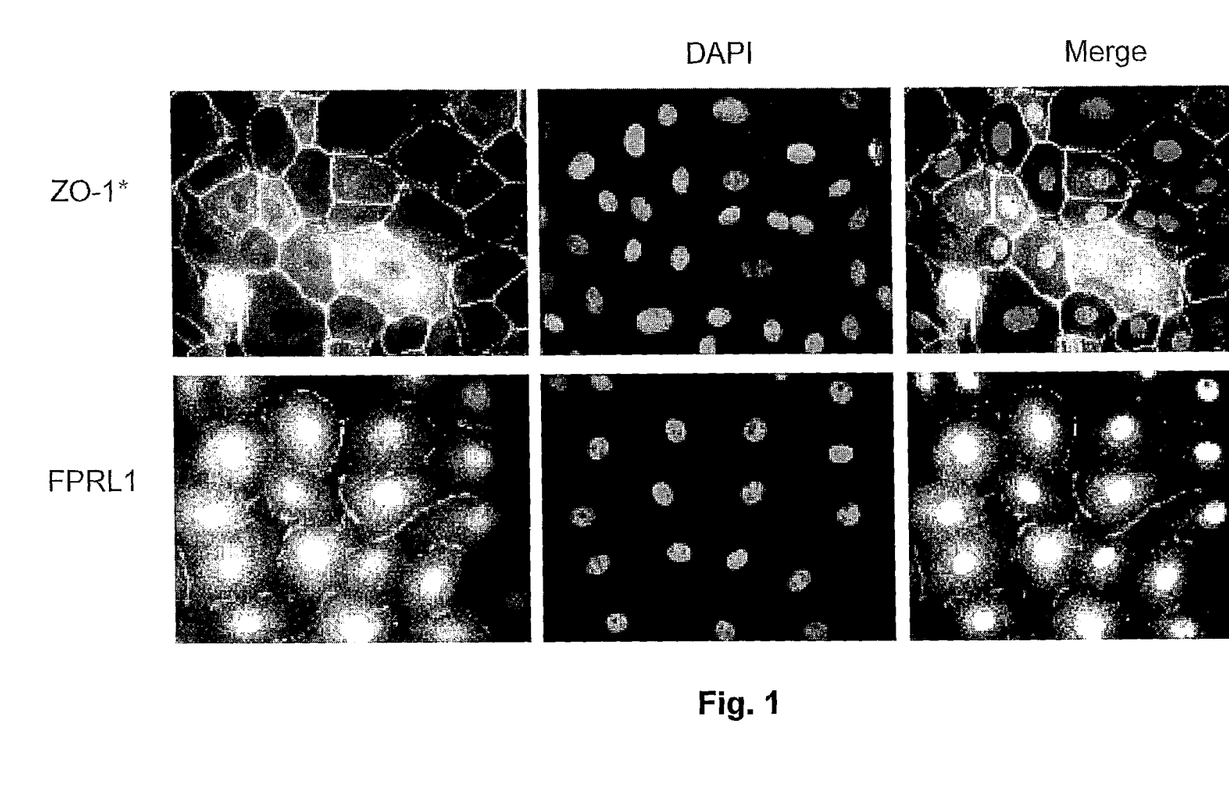
FIG. 1 illustrates the overlapping location of cornea endothelial cell phenotype (identified using the cell marker zona occludins-1 (ZO-1)) and of lipoxin A4 receptors (identified by the polyclonal antibody formyl peptide receptor-like 1 (FPRL1)) in rabbit corneal endothelial cells.

Rabbit corneal endothelial cells (RCEC) and human corneal endothelial cells along with the Decemet's membrane were isolated from normal eyes (National Disease Research Interchange (NDRI), Philadelphia, Pa.), and the cells were suspended in Dulbecco's Modified Eagle Medium/Nutrient Mixture F-12 (DMEM/F12; GIBCO®, Grand Island, N.Y.) supplemented with 15% fetal bovine serum (FBS; GIBCO®), and seeded in 12-well plates. Cell phenotype was identified by using the endothelial cell marker anti-ZO-1 antibody (anti-zonula occludins-1 antibody) (Zymed Laboratories, Inc., San Francisco, Calif.). The localization of the lipoxin A4 (LXA4) receptor was detected with the polyclonal antibody FPRL1 (formyl peptide receptor-like 1; sc-13193, Santa Cruz Biotechnology, Inc., Santa Cruz, Calif.) (FIG. 1). As shown in FIG. 1, RCEC possess the receptor for LXA4. The same was found with human endothelial cells. (Data not shown) This is the first time such receptor has been reported in cornea endothelial cells.

Example 2

Lipoxin A4 Promotes Proliferation of Corneal Endothelial Cells

Figure 2A:
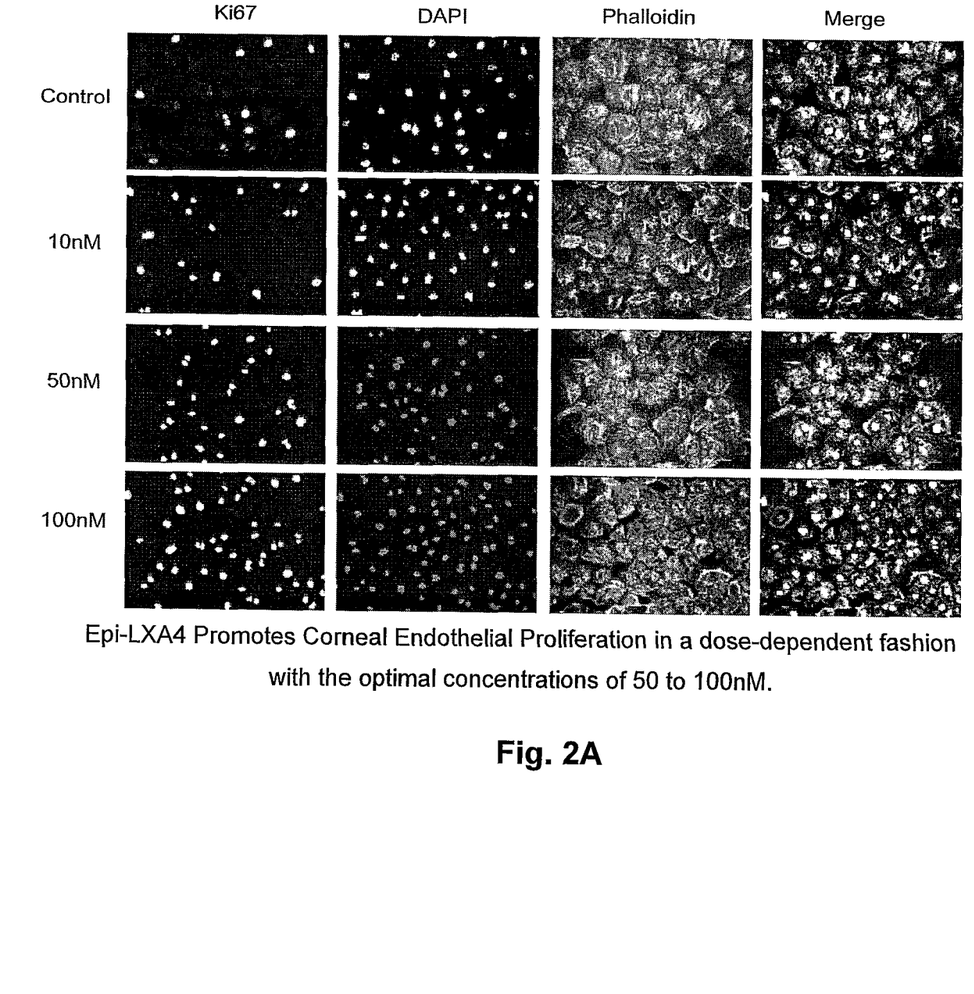
FIG. 2A illustrates the amount of corneal endothelial cell proliferation in rabbit corneal endothelial cells grown under various concentrations of 15-epimer lipoxin A4, with corneal endothelial cells identified with Ki-67 antibody staining.
Figure 2B:
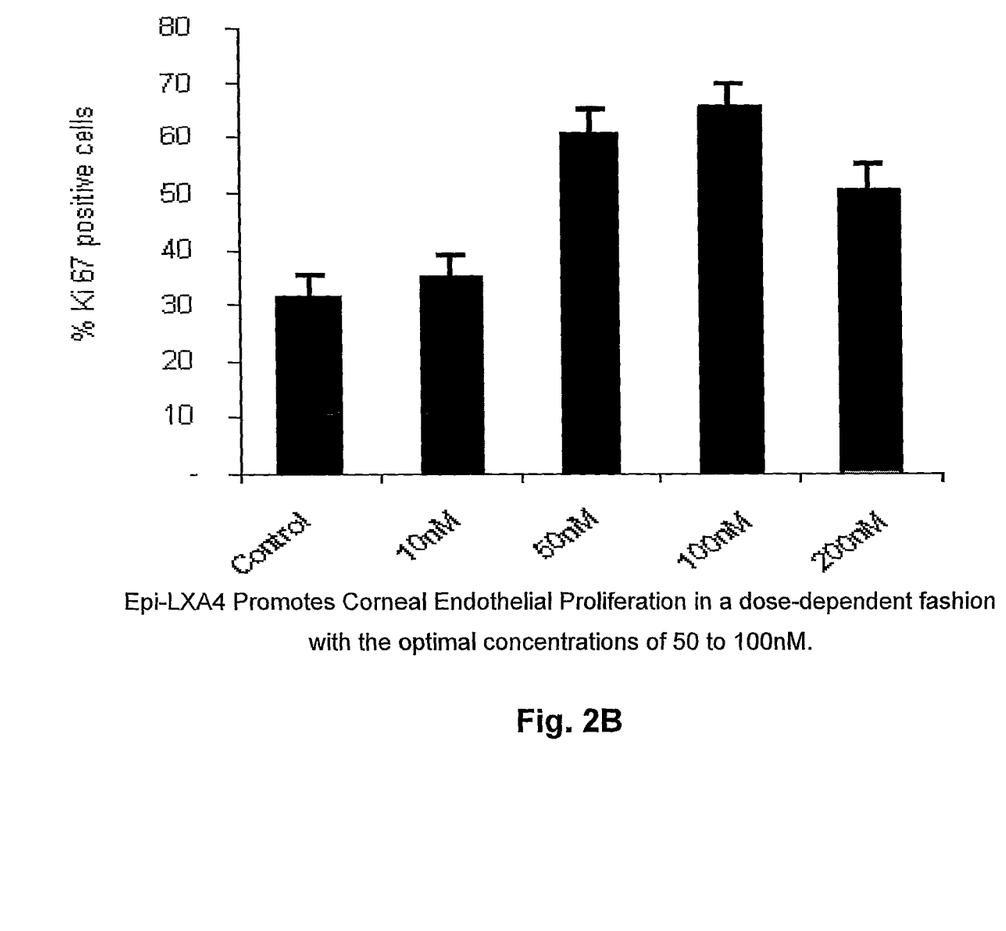
FIG. 2B illustrates the amount of corneal endothelial cell proliferation measured as percent Ki-67 antibody staining in rabbit corneal endothelial cells grown under various concentrations of 15-epimer lipoxin A4.

Proliferation of cornea endothelial cells was evaluated with anti-Ki-67 antibody (Zymed Laboratories, Inc., San Francisco, Calif.). Rabbit CEC cells were grown at 60-70% confluence, starved for 24 hours, and then treated with 15-epimer-lipoxin A4 (Calbiochem, Madison, Wis.) at different concentrations from 10 nM to 200 nM in DMEM/F12 containing 0.5% FBS for 24 hours. The results are shown in FIGS. 2A and 2B. As shown in FIGS. 2A and 2B, the number of cells with Ki-67 staining, indicating the number of cornea endothelial cells, increases with the concentration of epi-LXA4. In addition, a similar experiment was conducted using lipoxin A4. (Data not shown) The results using lipoxin A4 were the same, both qualitatively and quantitatively, as those shown in FIGS. 2A and 2B for the 15-epimer lipoxin A4. This indicates that LXA4 and its analog, 15-epimer lipoxin A4, promote the proliferation of corneal endothelial cells in a dose-dependent manner with optimal concentrations of 50 to 100 nM.

Example 3

Lipoxin A4 Promotes Cornea Endothelial Cell Integrity

Figure 3A:
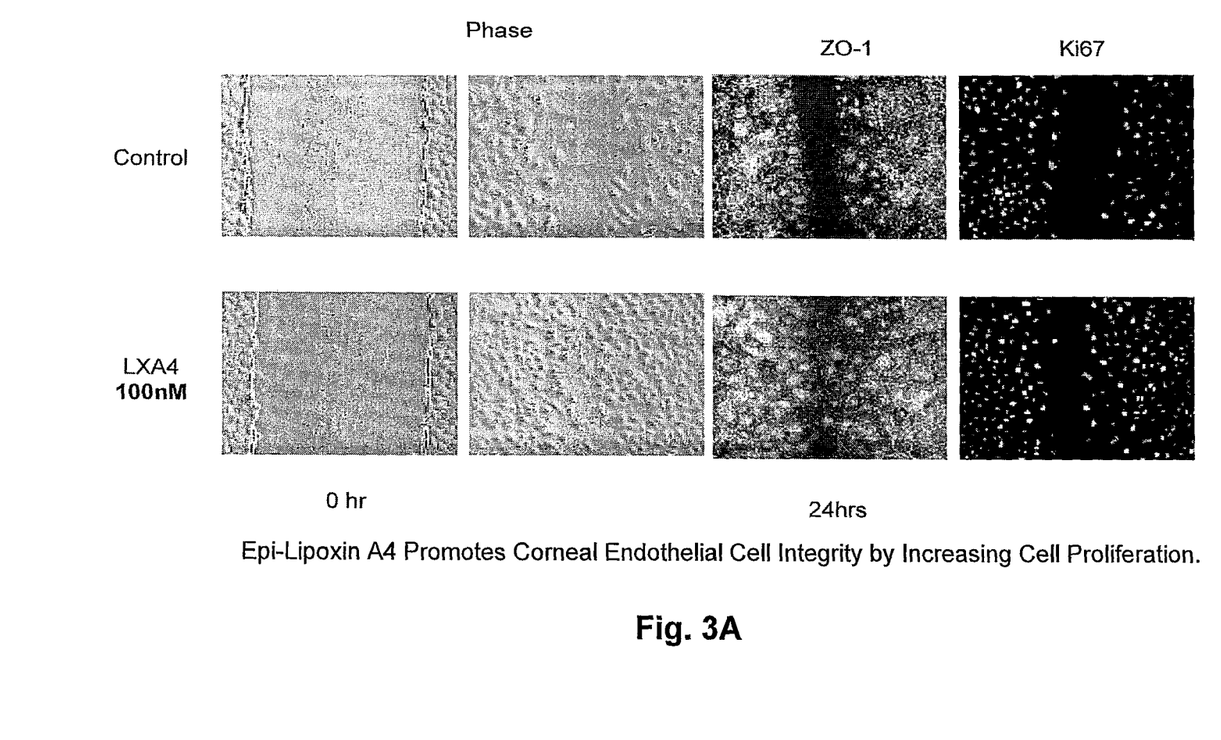
FIG. 3A illustrates the effect on wound closure in rabbit corneal endothelial cells after 24 hours by addition of 100 nM 15 epimer lipoxin A4, with corneal endothelial cells identified using the cell marker zona occludins-1 (ZO-1) and using Ki-67 antibody staining.
Figure 3B:
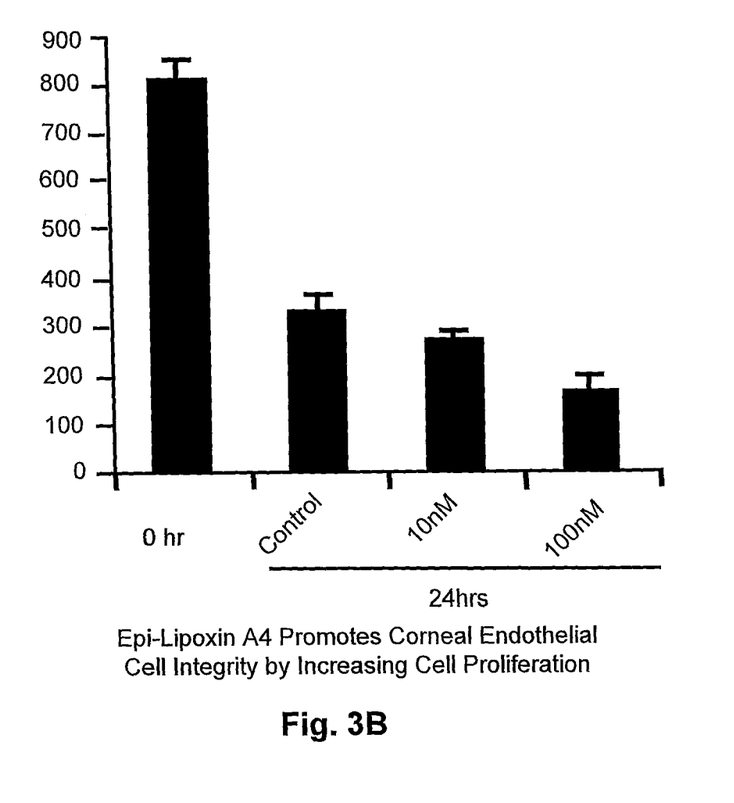
FIG. 3B gives the change in the width of a wound in rabbit corneal endothelial cells after 24 hours by the addition of 10 nM and 100 nM lipoxin A4 as calculated using phase contrast images seen in FIG. 3A and a Metavue Image software.

To measure in vitro wound closure, 12-day cultures of completely confluent RCEC in 12-well plates were wounded by linear scraping with a sterile plastic tip in the center of the well. Cells were incubated for 24 hours in DMEM/F12 with or without 15-epimer lipoxin A4 at 10 nM and 100 nM concentrations. Wound healing was determined by phase contrast images collected by a camera attached to the microscope as shown in FIG. 3A. The width of wound was calculated using Metavue Image software. Each point in FIG. 3B represents the analysis of images collected from 10 different wounded areas in two different wells. As shown in FIGS. 3A and 3B, 15-epimer lipoxin A4 promoted wound healing by increasing the number of cornea endothelial cells. This increase in endothelial cells would protect the cornea from swelling and loss of clarity. In addition, a similar experiment was conducted using lipoxin A4. (Data not shown) The results using lipoxin A4 were the same, both qualitatively and quantitatively, as those shown in FIGS. 3A and 3B for the 15-epimer lipoxin A4. This indicates that LXA4 and its analog, 15-epimer lipoxin A4, would promote wound healing and would protect the cornea from swelling and loss of clarity with optimal concentrations of 50 to 100 nM.

Example 4

In Vitro Culture of Human Corneal Endothelial Cells

Figure 4:
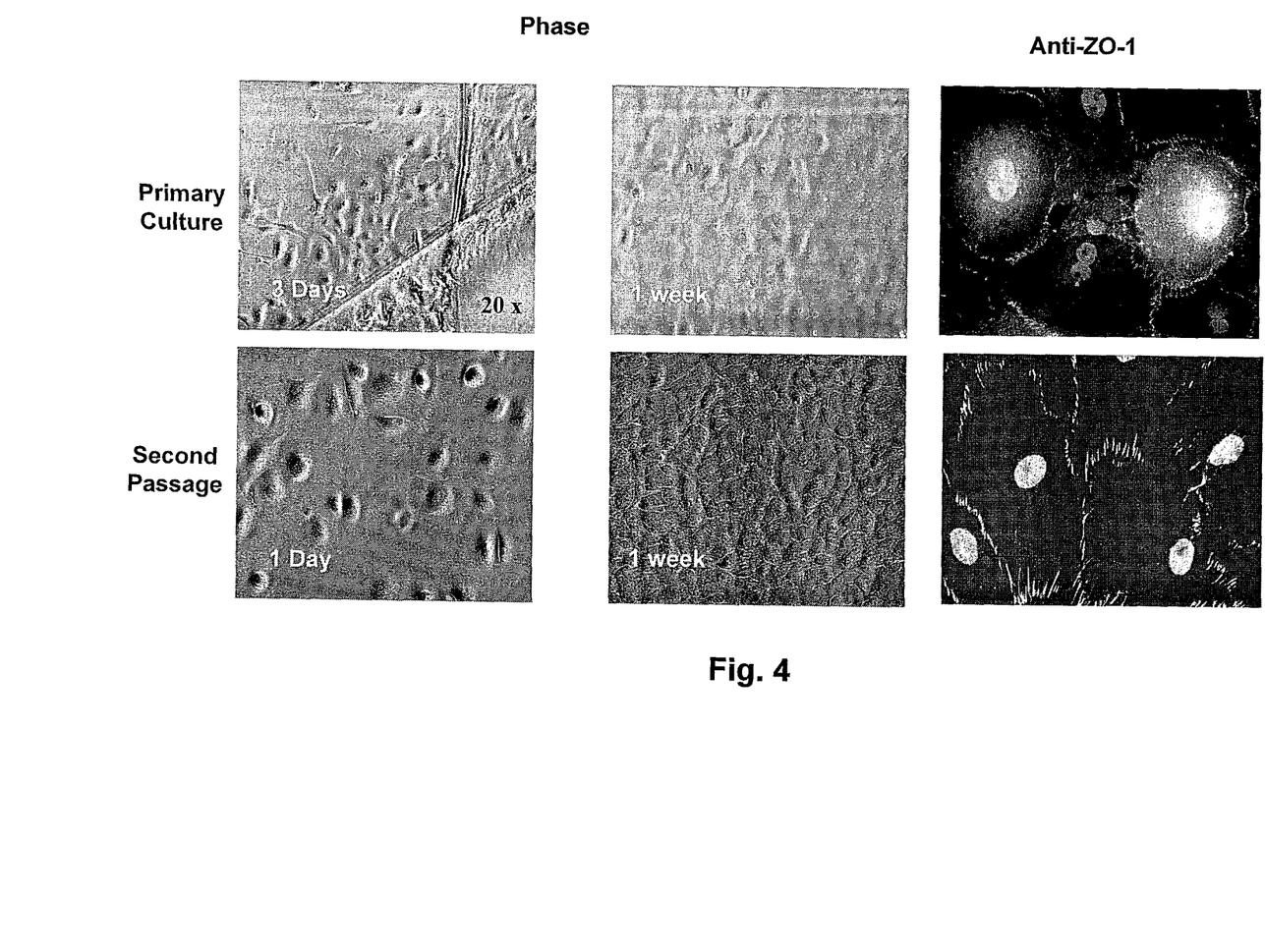
FIG. 4 illustrates human corneal endothelial cells grown in culture, both the primary culture and a second passage of cells, as identified using phase contrast microscopy and the endothelial cell marker anti-ZO-1 antibody.

Human eyeballs were obtained from NDRI (National Disease Research Interchange, Philadelphia, Pa.) and shipped to the laboratory on ice. The corneas were excised along the sclerocorneal rim, and the endothelia together with the Decemet's membrane were removed with tooth-free fine forceps under a dissection microscope. Pieces of the endothelia were seeded in DMEM/F12 (GIBCO®, Grand Island, N.Y.) supplemented with 15% FBS in 12-well plates. Cell phenotypes were identified and confirmed by using the endothelial cell marker anti-ZO-1 antibody (Zymed Laboratories, Inc., San Francisco, Calif.). FIG. 4 shows the primary culture and the second passage and confirms the presence of endothelial cells. This method of cell culture was used to establish cell cultures from several human eyeballs.

Example 5

Figure 5A:
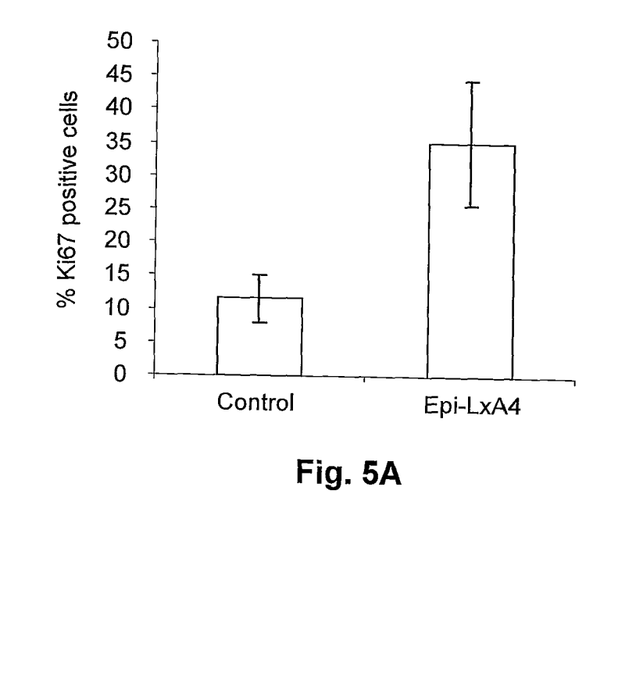
FIG. 5A illustrates the amount of corneal endothelial cell proliferation measured as mean percent Ki-67 antibody staining in human corneal endothelial cells grown in culture with and without 15 epimer lipoxin A4 (100 nM).
Figure 5B:
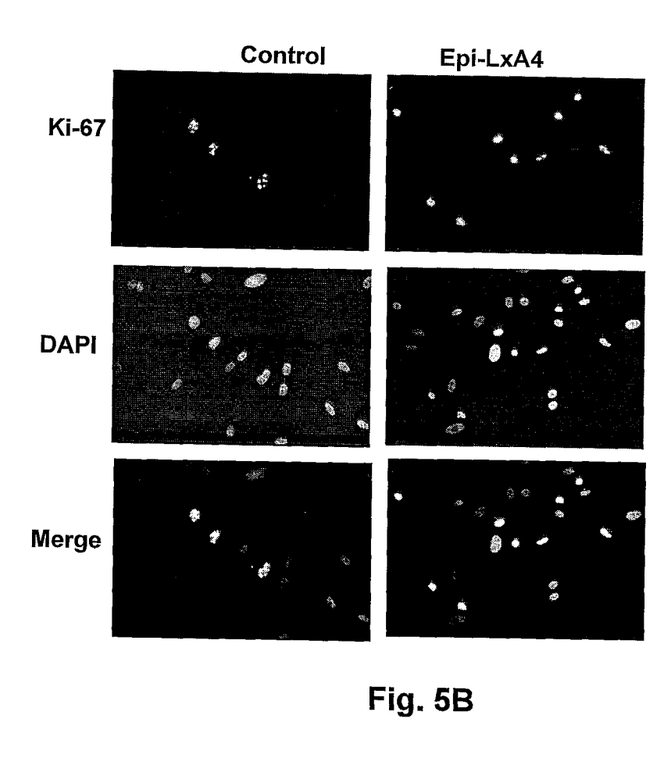
FIG. 5B illustrates the amount of corneal endothelial cell proliferation in human corneal endothelial cells grown in culture with and without 15-epimer lipoxin A4 (100 nM), using Ki-67 antibody to identify corneal endothelial cells.

Effect of Lipoxin A4 (an Epimer) on Cell Proliferation In Vitro Culture of Human Corneal Endothelial Cells A secondary passage of human corneal endothelial cells derived from a 40-year-old donor was obtained as described above in Example 4. The cells were grown to 70% confluence in 24-well plate, and then starved for 24 hours. The starved cells were then incubated in DMEM/F12 containing 0.5% FBS with or without 15-epimer LxA4 (100 nM; from Calbiochem, Madison, Wis.) for 24 hours. The degree of cell Proliferation was assayed by immunofluorescence staining with Ki-67 antibody, as shown in FIG. 5B. FIG. 5A shows the cell proliferation expressed as a mean+/−SD of percentages of Ki-67-positive cells versus total cells counted in 12 different fields of 4 wells. FIG. 5A shows a significant increase in human corneal endothelial cells in the presence of 15-epimer LxA4. Based on the rabbit studies above, it is believed that lipoxin A4 and its other analogs would show similar results as the 15-epimer lipoxin A4 used in these experiments.

Example 6

Figure 6A:
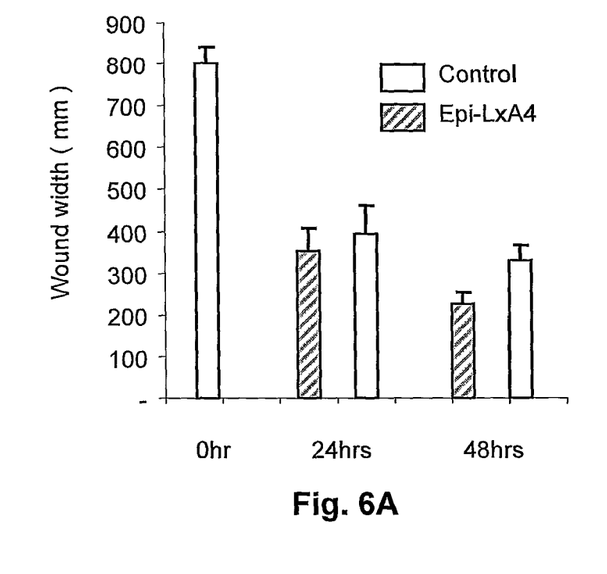
FIG. 6A illustrates the effect of 100 nM 15-epimer lipoxin A4 on cell migration, quantified by measuring the width of a wounded area in a human corneal endothelial cell culture at 24 and 48 hours.
Figure 6B:
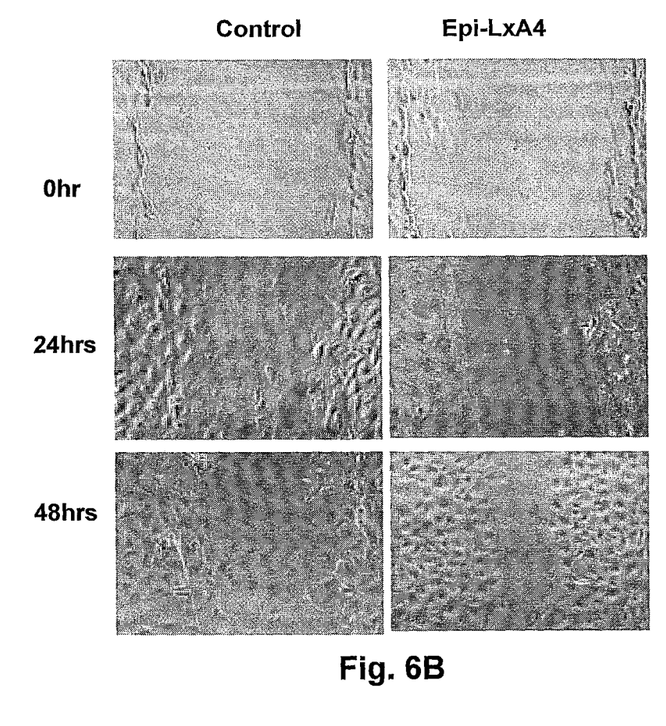
FIG. 6B illustrates the effect on wound closure in human corneal endothelial cells after 24 hours by addition of 100 nM 15 epimer lipoxin A4 as seen in phase contrast microscopy.

Effect of Lipoxin A4 on Cell Migration in a Wound of Human Corneal Endothelial Cells A secondary passage of human corneal endothelial cells derived from a 63-year-old donor was obtained as described above in Example 4. The cells were grown to 70% confluence in 24-well plate, and then starved for 24 hours. A linear wound was created in the center of the well with a sterile plastic tip, and the remaining cells were incubated in DMEM/F12 containing 0.5% FBS with or without 15-epimer LxA4 (100 nM) for 48 hours. Wound healing was determined by phase contrast images collected by a camera attached to the microscope, and the result shown in FIG. 6B. The width of wound was calculated using Metavue Image software. The degree of cell migration was quantified by measuring the width of the wounded area at 24 and 48 hours, and the data shown in FIG. 6A. The results in FIG. 6A represent mean+/− SD (n=12). As shown in FIGS. 6A and 6B, at 48 hours, a significant increase in cell migration was seen in the cell culture containing epi-LXA4. (*p<0.05) Based on the rabbit studies above, it is believed that lipoxin A4 and its other analogs would show similar results as the 15-epimer lipoxin A4 used in these experiments.

Miscellaneous

The term "lipoxin A4 analogs" is understood to be compounds that are similar in structure to lipoxin A4 and that exhibit a biologically qualitatively similar effect as the unmodified lipoxin A4. The term includes stereochemical isomers of lipoxin A4, e.g., the aspirin-triggered 15-epimer lipoxin A4, and other known analogs, e.g., ATLa2 and the 3-oxa-lipoxin analogs (e.g., ZK-994 and ZK-142). See, U.S. Pat. Nos. 6,831,186 and 6,645,978; I. M. Fierro et al., "Lipoxin A4 and aspirin-triggered 15-epi-lipoxin A4 inhibit human neutrophil migration: Comparisons between synthetic 15 epimers in chemotaxis and transmigration with microvessel endothelial cells and epithelial cells," Journal of Immunology, vol. 170, pp. 2688-2694 (2003); G. Bannenberg et al., "Lipoxins and novel 15-epi-lipoxin analogs display potent anti-inflammatory actions after oral administration," Brit. J. Pharma. Vol. 143, pp. 43-52 (2004); and R. Scalia et al., "Lipoxin A4 stable analogs inhibit leukocyte rolling and adherence in the rat mesenteric microvasculature: role of P-selectin," *Proc. Natl. Acad. Sci. USA*. vol. 94, pp. 9967-9972 (1997).

The term "effective amount" as used herein refers to an amount of lipoxin A4 or its analogs sufficient to promote the survival or proliferation of cornea endothelial cells in a cornea at risk for swelling or losing clarity, including a cornea in storage awaiting transplant, to a statistically significant degree ($p<0.05$). The term "effective amount" therefore includes, for example, an amount sufficient to promote the increase in cornea endothelial cells found in corneas placed in storage by at least 50%. The dosage ranges for the administration of lipoxin A4 or its analogs are those that produce the desired effect. Generally, the dosage will vary with the age and condition of the patient. A person of ordinary skill in the art, given the teachings of the present specification, may readily determine suitable dosage ranges. The dose of lipoxin A4 or its analog may be from 10 nM to 200 nM, but more preferably from 50 nM to 100 nM. In any event, the effectiveness of treatment can be determined by monitoring the number of cornea endothelial cells by methods well known to those in the field. Moreover, lipoxin A4 or its analogs can be applied in pharmaceutically acceptable carriers known in the art. The application can be oral, by injection, or topical, but the most preferred application is topically.

Lipoxin A4 or its analogs may be administered to a patient by any suitable means, including orally, parenteral, subcutaneous, intrapulmonary, topically, and intranasal administration. They may also be administered transdermally, for example in the form of a slow-release subcutaneous implant, or orally in the form of capsules, powders, or granules. The most preferred method will be topically or by an implant.

Lipoxin A4 or its analogs may be mixed with excipients that are pharmaceutically acceptable and are compatible with the active ingredient. Suitable excipients include water, saline, dextrose, glycerol and ethanol, or combinations thereof. Preservatives and other additives may also be present such as, for example, antimicrobials, anti-oxidants, chelating agents, inert gases, and the like.

Lipoxin A4 or its analogs may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of lipoxin A4 or its analogs may be controlled by altering the concentration of the macromolecule.

Another method for controlling the duration of action comprises incorporating lipoxin A4 or its analogs into particles of a polymeric substance such as a polyester, peptide, hydrogel, polylactide/glycolide copolymer, or ethylenevinylacetate copolymers. Alternatively, lipoxin A4 or its analogs may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

In addition, lipoxin A4 or its analogs could be administered using an implantable device, similar to a contact lens with a semipermeable membrane to permit the diffusion of the active lipoxin.

The present invention provides a method of promoting the survival or proliferation of cornea endothelial cells, comprising administering to a cornea or to a patient at risk for a cornea swelling or loss of clarity, an effective amount of lipoxin A4 or its analogs.

The complete disclosures of all references cited in this application are hereby incorporated by reference. In the event of an otherwise irreconcilable conflict, however, the present specification shall control.

What is claimed:

1. A sterile composition comprising an ex vivo cornea in storage prior to transplant, and a sterile solution comprising one or more compounds selected from the group consisting of lipoxin A4 and analogs of lipoxin A4.

2. The sterile composition of claim 1, wherein said sterile solution additionally comprises one or more compounds selected from the group consisting of indomethacin, epidermal growth factor, other growth factors, chondroitin sulfate, dextran 40, sodium bicarbonate, gentamycin, other antibiotics, amino acids, sodium pyruvate, and 2-mercaptoethanol.

3. The sterile composition of claim 1 wherein said sterile solution comprises lipoxin A4.

4. The sterile composition of claim 3, wherein the amount of said lipoxin A4 is from about 10 nM to about 200 nM.

5. The sterile composition of claim 3, wherein the amount of said lipoxin A4 is from about 50 nM to about 100 nM.

6. The sterile composition of claim 1, wherein said sterile solution comprises 15-epimer lipoxin A4.

7. The sterile composition of claim 6, wherein the amount of said 15-epimer lipoxin A4 is from about 10 nM to about 200 nM.

8. The sterile composition of claim 6, wherein the amount of said 15-epimer lipoxin A4 is from about 50 nM to about 100 nM.

* * * * *